(12) United States Patent
Lorant

(10) Patent No.: US 6,395,285 B1
(45) Date of Patent: May 28, 2002

(54) ANHYDROUS COMPOSITION CONTAINING A VOLATILE FLUORO COMPOUND, AND USES THEREOF, IN PARTICULAR COSMETIC USES

(75) Inventor: Raluca Lorant, Thiais (FR)

(73) Assignee: L'Oreal, Paris (FR)

( * ) Notice: Subject to any disclaimer, the term of this patent is extended or adjusted under 35 U.S.C. 154(b) by 78 days.

(21) Appl. No.: 09/684,620

(22) Filed: Oct. 10, 2000

(30) Foreign Application Priority Data

Oct. 27, 1999 (FR) .............................. 99 13448

(51) Int. Cl.$^7$ .............................. A61K 7/00; A61K 7/42; A61K 7/44
(52) U.S. Cl. .............................. 424/401; 424/59; 424/60; 424/400; 424/401
(58) Field of Search .............................. 424/59, 60, 400, 424/401

(56) References Cited

FOREIGN PATENT DOCUMENTS

EP              0 850 643              7/1998

OTHER PUBLICATIONS

Minoru Onaki et al, "Makeup powders containing fluoro compounds and organopolysiloxanes", Chemical Abstract No. XP–002143417, AN 129:152997 CA.

Primary Examiner—Shelley A. Dodson
(74) Attorney, Agent, or Firm—Oblon, Spivak, McClelland, Maier & Neustadt, P.C.

(57) ABSTRACT

An anhydrous cosmetic composition comprising, in a fatty phase, at least one elastomeric, solid polyorganosiloxane which is at least partially cross-linked and at least one volatile fluoro oil with a density of greater than 1.

20 Claims, No Drawings

ANHYDROUS COMPOSITION CONTAINING A VOLATILE FLUORO COMPOUND, AND USES THEREOF, IN PARTICULAR COSMETIC USES

BACKGROUND OF THE INVENTION

1. Field of the Invention

The present application relates to an anhydrous composition comprising, in a fatty phase, at least one crosslinked elastomeric solid polyorganosiloxane and at least one volatile fluoro oil with a density of greater than 1, and to the use of the composition, in particular, in cosmetics for treating, protecting, caring for, removing make-up from and/or cleansing the skin, the lips and/or the hair, and/or for making up the skin and/or the lips.

2. Description of the Background

Anhydrous compositions constitute excellent cosmetic or dermatological supports, in particular, as vehicles for active agents. These compositions thus make it possible to form a lipid film at the surface of the skin, which prevents transepidermal water loss and protects the skin against external attack. However, these compositions have the drawback of lacking in comfort and cosmetic pleasantness since, because of the absence of water, they lack a fresh sensation and appear particularly heavy and uncomfortable, even when they do not contain any nourishing oils known to give a greasy effect.

In order to overcome this disadvantage, the known practice has been to incorporate gels based on crosslinked elastomeric organosiloxanes, such as those described in U.S. Pat. No. 4,987,168, into anhydrous compositions. These gels improve the cosmetic qualities of these compositions, in particular by providing softness, a matt effect and a less greasy feel.

However, although the compositions obtained appear to be less greasy, they lack a fresh sensation when they are applied to the skin. A need continues to exist for anhydrous compositions for topical application which provide for an increased fresh and soft feeling when applied to the skin.

SUMMARY OF THE INVENTION

Accordingly, one object of the present invention is to provide an anhydrous composition for topical application which results in an improved feeling of freshness and softness upon application to the skin.

Briefly, this object and other objects of the present invention as hereinafter will become more readily apparent can be attained by an anhydrous composition which comprises, in a fatty phase, at least one elastomeric solid polyorganosiloxane which is at least partially cross-linked and at least one volatile fluoro oil having a density of greater than 1.

DETAILED DESCRIPTION OF THE PREFERRED EMBODIMENTS

It has now been discovered, unexpectedly, that the use of a volatile fluoro oil with a density of greater than 1 in an anhydrous composition allows the preparation of anhydrous compositions which have very good cosmetic properties and which provide a sensation of freshness and comfort when they are applied to the skin, which is not obtained with the compositions known in the art.

The term "fatty phase" as used in the present text means a phase comprising fatty substances and in particular oils.

According to the invention, the density of the volatile fluoro oil component of the composition is generally greater than about 1.1 and preferably greater than 1.2.

The expression "volatile fluoro oil" should be understood as meaning an oil having, at 25° C., a saturating vapor pressure at least equal to 50 Pa.

Suitable volatile fluoro oils which satisfy the above density and vapor pressure criteria include the following fluoro compounds:

1) perfluorocycloalkyls having formula (I) below:

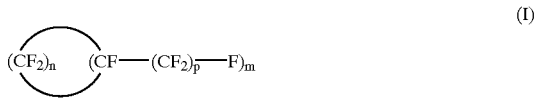

(I)

in which n is 4 or 5, m is 1 or 2, and p is 1, 2 or 3, with the proviso that, when m=2, the groups are not necessarily alpha to each other;

2) perfluoroalkanes having formula (II) below:

(II)

in which m is 2 to 8, and X represents Br or F;

3) fluoroalkyls or heterofluoroalkyls having formula (III) below:

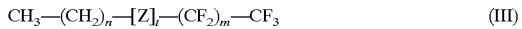

(III)

in which t is 0 or 1, n is 0, 1, 2 or 3, m is 2, 3, 4 or 5, and Z is O, S or NR, wherein R is hydrogen or a $-(CH_2)_p-CH_3$ group or a $-(CF_2)_p-CF_3$ group, wherein p is 2, 3, 4 or 5; and 4) perfluoromorpholine derivatives having formula (IV) below:

(IV)

in which R is a $C_1-C_4$ perfluoroalkyl radical.

Suitable perfluorocycloalkyl compounds of formula (I) include, in particular, perfluoromethylcyclopentane and perfluoro-1,3-dimethylcyclohexane, which are sold under the names "Flutec PC1®" and "Flutec PC3®" by the company BNFL Fluorochemicals Ltd., which have respective densities of 1.26 and 1.82, as well as perfluoro-1,2-dimethylcyclobutane.

Suitable perfluoroalkane compounds of formula (II) include, inter alia, dodecafluoropentane and tetradecafluorohexane, which are sold under the names "PF 5050®" and "PF 5060®" by the company 3M and which have respective densities of 1.63 and 1.68, or alternatively bromoperfluorooctyl sold under the name "Foralkyl®" by the company Atochem, which has a density of 1.95.

Suitable fluoro compounds of formula (III) include, for example, nonafluoromethoxybutane, sold under the name "MSX 4518®" by the company 3M, which has a density of 1.53, and nonafluoroethoxyisobutane, which has a density of 1.43.

Finally, suitable perfluoromorpholine derivatives include, for example, 4-trifluoromethylperfluoromorpholine, sold by the company 3M under the name "PF 5052®", with a density equal to 1.7.

The fluoro compounds as described above are moreover characterized by a boiling point generally ranging from 25 and 65° C.

The amount of volatile fluoro oil in the composition of the invention can vary over a wide range and generally ranges from 0.5% to 60%, preferably from 5% to 50% by weight relative to the total weight of the composition.

The composition of the invention contains at least one at least partially crosslinked elastomeric solid polyorganosiloxane. The term "elastomer" means a flexible, deformable material which has viscoelastic properties and in particular the consistency of a sponge or a supple sphere. Its modulus of elasticity is such that this material withstands deformation and has a limited capacity to extension and contraction. This material is capable of regaining its original shape after it has been stretched. This elastomer is formed from high molecular weight polymer chains whose mobility is limited by a uniform network of crosslinking points.

The elastomeric polyorganosiloxanes used in the composition of the invention are partially or totally crosslinked. When included in an oily phase, they become transformed, depending on the amount of oily phase used, from a product of spongy appearance when they are used in the presence of small amounts of oily phase, into a homogeneous gel in the presence of larger amounts of oily phase. The gelation of the oily phase with these elastomers may be total or partial.

The elastomers of the invention can be conveyed in the form of a gel consisting of an elastomeric polyorganosiloxane, including at least one hydrocarbon-based oil and/or one silicone oil and/or one fluoro oil. Thus, the oily phase associated with the elastomeric polyorganosiloxane can consist of this or these oils.

The elastomeric polyorganosiloxanes used in the invention can be selected from the crosslinked polymers described in European Patent Application Number 0 295 886. According to the application, the elastomeric polyorganosiloxanes are prepared by addition reactions and crosslinking, in the presence of a platinum-type catalyst, of at least:

(a) one polyorganosiloxane containing at least two lower alkenyl groups per molecule, these alkenyl groups containing two to six carbon atoms; and (b) one polyorganosiloxane containing at least two hydrogen atoms linked to a silicon atom per molecule.

The elastomeric polyorganosiloxanes used in the composition of the invention can also be selected from those described in U.S. Pat. No. 5,266,321. According to the patent, the elastomeric polyorganosiloxanes are selected, in particular, from:

i) polyorganosiloxanes comprising $R_2SiO$ and $RSiO_{1.5}$ units and optionally $R_3SiO_{0.5}$ and/or $SiO_2$ units, in which the radicals R, independently of each other, represent hydrogen, an alkyl radical such as methyl, ethyl or propyl, an aryl radical such as phenyl or tolyl, or an unsaturated aliphatic group such as vinyl, the weight ratio of the units $R_2SiO$ to the units $RSiO_{1.5}$ ranging from 1/1 to 30/1;

ii) polyorganosiloxanes which are insoluble and swellable in silicone oil, prepared by combining an organohydrogenopolysiloxane (1) and a polyorganosiloxane (2) containing unsaturated aliphatic groups, such that the amount of hydrogen or of unsaturated aliphatic groups in (1) and (2) respectively ranges from 1 to 20 mol. % when the polyorganosiloxane is non-cyclic and from 1 to 50 mol. % when the polyorganosiloxane is cyclic.

The polyorganosiloxanes in the composition of the invention are, for example, those sold under the names KSG 6 from Shin Etsu, Trefil E-505C or Trefil E-506C from Dow Corning, Gransil (SR-CYC, SR DMF10, SR-DC556) from Grant Industries, or those sold in the form of preconstituted gels: KSG 15, KSG 17, KSG 16, KSG 18, KSG 26A and KSG 26B from Shin Etsu, Gransil SR 5CYC gel, Gransil SR DMF 10 gel and Gransil SR DC556 gel from Grant Industries, and 1229-02-167 and 1229-02-168 from General Electric. A mixture of these commercial products can also be used.

The elastomeric polyorganosiloxane(s) used in the invention is(are) preferably present in an active material concentration ranging from 0.1% to 20%, preferably from 0.5% to 15% and better still from 1.5% to 15% relative to the total weight of the composition.

The oily phase employed in the manufacture of the elastomeric polyorganosiloxane anhydrous gel contains one or more oils which are liquid at room temperature (25° C.), selected from hydrocarbon-based oils and/or silicone oils. The oily phase is advantageously a silicone liquid phase containing one or more oils selected from polydimethylsiloxanes containing a linear or cyclic chain, which are liquid at room temperature, optionally comprising an alkyl or aryl chain which is pendant or at the end of the chain, the alkyl chain containing from 1 to 6 carbon atoms.

Besides the oils optionally present in the elastomeric polyorganosiloxane gel, the fatty phase in the composition of the invention can be of any nature and can comprise oils, waxes or gums that are solid at room temperature, pasty fatty substances, of animal, plant, mineral or synthetic origin, and mixtures thereof.

Suitable oils which can be used in the composition of the invention include, in particular:

hydrocarbon-based oils of animal origin, such as perhydrosqualene;

hydrocarbon-based oils of plant origin, such as liquid triglycerides of fatty acids, for example sunflower oil, corn oil, soybean oil, marrow oil, grapeseed oil, sesame oil, hazelnuts oil, apricot kernel oil, macadamia oil, castor oil, avocado oil, the liquid fraction of karite butter, caprylic/capric acid triglycerides such as those sold by the company Stearineries Dubois or those sold under the names Miglyol 810, 812 and 818 by the company Dynamit Nobel;

oils of formula $R^1COOR^2$ in which $R^1$ represents a higher fatty acid residue containing from 7 to 19 carbon atoms and $R^2$ represents a branched hydrocarbon-based chain containing from 3 to 20 carbon atoms, such as, for example, purcellin oil, isopropyl myristate or alkyl or polyalkyl octanoates, decanoates or ricinoleates;

linear or branched hydrocarbons of mineral or synthetic origin, such as volatile or non-volatile liquid paraffins and derivatives thereof, for instance hydrogenated isoparaffin, petroleum jelly, polydecenes and hydrogenated polyisobutene such as parleam;

synthetic ethers of formula $R^3OR^4$ in which $R^3$ is a $C_3$ to $C_{20}$ alkyl radical and $R^4$ is a $C_3$ to $C_{20}$ alkyl radical;

fatty alcohols such as octyldodecanol or oleyl alcohol;

partially hydrocarbon-based and/or silicone-based fluoro oils, for instance perfluoropolyesters;

silicone oils such as polymethylsiloxanes containing a linear or cyclic silicone chain, which are liquid or pasty at room temperature, such as cyclomethicones, in particular cyclohexamethicone and cyclopentamethicone; phenyldimethicones, phenyltrimethicones, polymethylphenylsiloxanes and alkylpolydimethylsiloxanes containing a $C_2$ to $C_{20}$ alkyl chain; and mixtures thereof.

The composition of the invention may be especially suitable for topical use and can constitute in particular a cosmetic or dermatological composition. In this case, it contains a physiologically acceptable medium. The expression "physiologically acceptable" means a medium which is compatible with the skin, the eyes and the keratin fibres (hair, eyelashes) of human beings.

In a known manner, the compositions of the invention can contain adjuvants that are common in the fields under consideration, such as active agents, lipophilic gelling agents, preserving agents, antioxidants, fragrances, solvents, fillers, screening agents, dyestuffs, acidic or basic agents and lipid vesicles. These adjuvants are used in the usual proportions in the fields under consideration, and, for example, from 0.01% to 20% relative to the total weight of the composition. These adjuvants and their concentrations should be such that they do not modify the property desired for the composition of the invention.

Lipophilic gelling agents which may be mentioned are modified clays such as bentones, metal salts of fatty acids, hydrophobic silica and polyethylenes.

Active agents which may be mentioned in particular are lipophilic active agents such as liposoluble sunscreens, for instance octyl methoxycinnamate; vitamins and in particular vitamins A, E, F and D and derivatives thereof, for instance vitamin A palmitate, 7-dehydrocholesterol or provitamin D3, and tocopheryl acetate; unsaturated fatty acids such as linoleic acid and linolenic acid; α-bisabolol; butters of plant origin mentioned above among the oils, for instance shorea butter or karite butter, which reconstitute the lipid barrier of the skin and allow the treatment of dry skin.

Moreover, the composition of the invention has the advantage of stabilizing any active agent, in particular a hydrophilic active agent, which is unstable in an oxidative medium, and mention may be made in particular, as active agents that are unstable in an oxidative medium, of vitamins and in particular ascorbic acid (vitamin C) and its derivatives, in particular its glycosyl and phosphate derivatives, and its esters, for instance ascorbyl acetate, palmitate and propionate, retinol (vitamin A) and its derivatives, in particular its esters, for instance retinyl acetate and propionate; urea; rutin; enzymes such as lipase, protease, phospholipase and cellulases; natural extracts such as green tea, extract of balm, extract of thyme, procyannidol oligomers (PCOS) such as hawthorn PCO, pine PCO and grape PCO; certain acids such as kojic acid, caffeic acid, retinoic acid and its derivatives, benzene-1,4-bis(3-methylidene-10-camphorsulfonic acid); carotenoids such as carotenes, for instance α-, β- and γ-carotenes, β, φ-carotene, ζ-carotene, β, λ-carotene, lycopene (ψ,ψ-carotene); polyunsaturated fatty acids such as gammalinolenic acid, and mixtures thereof.

Also included as ingredients of the present composition are any natural or synthetic compound which may contain one or more of the active agents indicated above, in particular plant extracts. and more especially fruit extracts.

Suitable fillers which can be used in the composition of the invention include, for example, talc; polyamide particles and in particular those sold under the name Orgasol by the company Atochem; polyethylene powders; microspheres based on acrylic copolymers, such as those made of ethylene glycol dimethacrylate/lauryl methacrylate copolymer, sold by the company Dow Coming under the name Polytrap; expanded powders such as hollow microspheres, and in particular the microspheres sold under the trade name Expancel by the company Kemanord Plast or under the trade name Micropearl F 80 ED by the company Matsumoto; powders of natural organic materials such as crosslinked or non-crosslinked corn, wheat or rice starches, for instance the search powders crosslinked with octenylsuccinic anhydride, sold under the name Dry-Flo by the company National Starch; silicone resin microbeads such as those sold under the name Tospearl by the company Toshiba Silicone; and mixtures thereof.

The composition which is the subject of the invention finds its application in particular in a large number of cosmetic treatments for the skin, the lips and the hair, including the scalp, in particular for treating, protecting, caring for, removing make-up from and/or cleansing the skin, the lips and/or the hair, and/or for making up the skin and/or the lips. It may also be used for treating dry skin and/or dry lips.

The composition of the invention can be used, for example, as a care product, a make-up-removing product and/or a cleansing product for the face in the form of a cream or milk, as a make-up product (for the skin and lips) by incorporation of fillers or dyes, or as protective antisun products by incorporation of screening agents.

Thus, an aspect of the invention is also the cosmetic use of the composition as defined above for treating, protecting, caring for, removing make-up from and/or cleansing the skin, the lips and/or the hair, and/or for making up the skin and/or the lips.

An additional aspect of the invention is a process for cosmetically treating the skin, including the scalp, the hair and/or the lips, by applying a composition as defined above to the skin, the hair and/or the lips.

Still another aspect of the invention is the use of the composition as defined above for the manufacture of a composition intended for caring for dry skin and/or dry lips.

Having now generally described this invention, a further understanding can be obtained by reference to certain specific Examples which are provided herein for purposes of illustration only and are not intended to be limiting unless otherwise specified. The amounts indicated are percent by weight, except where otherwise mentioned.

EXAMPLES

| Example 1: Repairing balm for the lips | |
|---|---|
| Gelled phase: | |
| KSG 6 (dimethicone/vinyl dimethicone crosspolymer containing 60% active material in dimethicone) | 50% |
| Hydrogenated isoparaffin | 43% |
| Liquid fraction of karite butter | 2% |
| Fluoro phase: | |
| Nonafluoromethoxybutane (MSX 4518 from the company 3M) | |

Procedure

The fluoro phase is dispersed in the gelled phase. A gel is obtained which is particularly soft and pleasant to apply and which immediately makes the lips smooth.

| Example 2: Softening powdery cream | |
|---|---|
| Gelled phase: | |
| KSG 16 (dimethicone/vinyl dimethicone crosspolymer containing 24% active material in dimethicone) | 40% |
| Apricot kernel oil | 10% |

-continued

Example 2: Softening powdery cream

| | |
|---|---|
| Cyclohexamethicone | qs 100% |
| Fillers | |
| Nylon-12 powder (Orgasol 2002 from the company Atochem) | 5% |
| Talc | 16% |
| Fluoro phase: | |
| Tetradecafluorohexane (PF 5060 from the company 3M) | 20% |

Procedure

The fillers are dispersed in the gelled phase and the fluoro phase is then dispersed in the mixture obtained.

A powdery unctuous cream which feels very soft and light when applied is obtained.

The disclosure of French priority Application Number 9913448 filed Oct. 27, 1999, is hereby incorporated by reference into the present application.

Obviously, numerous modifications and variations of the present invention are possible in light of the above teachings. It is, therefore, to be understood that within the scope of the appended claims, the invention may be practiced otherwise than as specifically described herein

What is claimed as new and is intended to be secured by letters Patent is:

1. An anhydrous cosmetic composition comprising, in a fatty phase, at least one elastomeric, solid polyorganosiloxane which is at least partially cross-linked and at least one volatile fluoro oil with a density of greater than 1.

2. The anhydrous cosmetic composition according to claim 1, wherein the volatile fluoro oil has a density of greater than 1.2.

3. The anhydrous cosmetic composition according to claim 1, wherein the volatile fluoro oil is a perfluorocycloalkyl having formula (I) below:

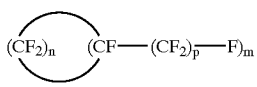
(I)

wherein n is 4 or 5, m is 1 or 2, and p is 1, 2 or 3, with the proviso that when m=2, the groups are not necessarily alpha to each other.

4. The anhydrous cosmetic composition according to claim 1, wherein the volatile fluoro oil is a perfluoroalkane having formula (II) below:

$$CF_3-(CF_2)_m-CF_2X \quad (II)$$

wherein m is 2 to 8, and X represents Br or F.

5. The anhydrous cosmetic composition according to claim 1, wherein the volatile fluoro oil is a fluoroalkyl or heterofluoroalkyl having formula (III) below:

$$CH_3-(CH_2)_m-[Z]_t-(CF_2)_m-CF_3 \quad (III)$$

wherein t is 0 or 1, n is 0, 1, 2 or 3, m is 2, 3, 4 or 5, and Z is O, S or NR, wherein R is hydrogen or a —(CH$_2$)$_p$—CH$_3$ or —(CF$_2$)$_p$—CF$_3$ radical, wherein p is 2, 3, 4 or 5.

6. The anhydrous cosmetic composition according to claim 1, wherein the volatile fluoro oil is a perfluoromorpholine derivative having formula (IV) below:

in which R is a $C_1$–$C_4$ perfluoroalkyl radical.

7. The anhydrous cosmetic composition according to claim 1, wherein the volatile fluoro oil is selected from the group consisting of perfluoromethylcyclopentane, perfluoro-1,3-dimethylcyclohexane, dodecafluoropentane, tetradecafluorohexane, bromoperfluorooctyl, nonafluoromethoxybutane, nonafluoroethoxyisobutane and 4-trifluoromethylperfluoromorpholine.

8. The anhydrous cosmetic composition according to claim 1, wherein the content of volatile fluoro oil ranges from 0.5% to 60% by weight relative to the total weight of the composition.

9. The anhydrous cosmetic composition according to claim 1, wherein the elastomeric polyorganosiloxane is prepared by an addition reaction and crosslinking, in the presence of a catalyst, of at least:

(a) one polyorganosiloxane containing at least two lower alkenyl groups per molecule; and (b) one polyorganosiloxane containing at least two hydrogen atoms linked to a silicon atom per molecule.

10. The anhydrous cosmetic composition according to claim 1, wherein the polyorganosiloxane is selected from the group consisting of:

i) polyorganosiloxanes comprising $R_2SiO$ and $RSiO_{1.5}$ units and optionally $R_3SiO_{0.5}$ and/or $SiO_2$ units, in which the radicals R, independently of each other, represent a hydrogen, an alkyl radical, an aryl radical, or an unsaturated aliphatic group, the weight ratio of the units $R_2SiO$ to the units $RSiO_{1.5}$ ranging from 1/1 to 30/1;

ii) polyorganosiloxanes which are insoluble in silicone oil, obtained by adding an organohydrogenopolysiloxane (1) and a polyorganosiloxane (2) containing unsaturated aliphatic groups, such that the amount of hydrogen or of unsaturated aliphatic groups in (1) and (2) respectively ranges from 1 to 20 mol. % when the polyorganosiloxane is non-cyclic and from 1 to 50 mol. % when the polyorganosiloxane is cyclic.

11. The anhydrous cosmetic composition according to claim 1, wherein the elastomeric solid polyorganosiloxane is present in an active material concentration ranging from 0.1% to 20% by weight relative to the total weight of the composition.

12. The anhydrous cosmetic composition according to claim 11, wherein the concentration of elastomeric solid polyorganosiloxane ranges from 0.5% to 15%.

13. The anhydrous cosmetic composition according to claim 1, wherein the fatty phase contains oils, waxes, gums or pasty fatty substances or mixtures thereof.

14. The anhydrous cosmetic composition according to claim 13, wherein the oil of said fatty phase is a member selected from the group consisting of hydrocarbon oils of animal origin, hydrocarbon oils of plant origin, oils having the formula $R^1COOR^2$, wherein $R^1$ is a higher fatty acid residue containing from 7 to 19 carbon atoms and $R^2$ is a branched hydrocarbon chain containing from 3 to 20 carbon atoms, linear or branched hydrocarbon of mineral or synthetic origin, synthetic ethers of formula $R^3OR^4$, wherein $R^3$ is a 3 to 19 carbon atom content alkyl group and $R^4$ is a 3 to 20 carbon atom content alkyl group, fatty alcohols, partially hydrocarbon-based and/or silicone-based fluoro oils, silicone oils and mixtures thereof.

15. A method of cleansing the skin or removing make-up from the skin, lips or eye lashes, comprising:

applying the anhydrous cosmetic composition of claim 1 to the skin, lips or eye lashes and thereby effecting skin cleansing and make-up removal.

16. A method of treating, protecting or caring for the skin, lips or eye lashes, comprising:

applying the anhydrous cosmetic composition of claim 1 to the skin, lips or eye lashes thereby effecting said treatment, protection of or caring for the skin, lips or eye lashes.

17. A method of treating dry skin or lips, comprising:

applying the anhydrous cosmetic composition of claim 1 to the skin or lips thereby effecting said treatment.

18. The method of claim 16, wherein the composition, in the form of a care product, a make-up removing product and a cleansing product, is in the form of a cream or milk.

19. A make-up composition comprising the composition of claim 1, at least one filler or a dye.

20. A sunlight screening composition comprising the composition of claim 1 and a sun screening agent.

* * * * *